United States Patent
Averkiou et al.

(10) Patent No.: US 8,529,453 B2
(45) Date of Patent: Sep. 10, 2013

(54) RESPIRATORY-GATED THERAPY ASSESSMENT WITH ULTRASONIC CONTRAST AGENTS

(76) Inventors: Michalakis Averkiou, Lakatamia (CY); Marios Lampaskis, Nicosia (CY); Konstantina Kyriakopoulou, Athens (GR)

( * ) Notice: Subject to any disclaimer, the term of this patent is extended or adjusted under 35 U.S.C. 154(b) by 254 days.

(21) Appl. No.: 12/864,273

(22) PCT Filed: Jan. 23, 2009

(86) PCT No.: PCT/IB2009/050277
§ 371 (c)(1),
(2), (4) Date: Jul. 23, 2010

(87) PCT Pub. No.: WO2009/093212
PCT Pub. Date: Jul. 30, 2009

(65) Prior Publication Data
US 2010/0298706 A1    Nov. 25, 2010

Related U.S. Application Data

(60) Provisional application No. 61/022,888, filed on Jan. 23, 2008.

(51) Int. Cl.
*A61B 8/14*    (2006.01)
*A61B 8/00*    (2006.01)

(52) U.S. Cl.
USPC .......................................... 600/458; 600/443

(58) Field of Classification Search
USPC ................... 600/437, 443, 458; 382/128
See application file for complete search history.

(56) References Cited

U.S. PATENT DOCUMENTS
| | | |
|---|---|---|
| 6,659,953 B1 | 12/2003 | Sumanaweera et al. |
| 2004/0120559 A1 | 6/2004 | Hall |
| 2005/0033179 A1 | 2/2005 | Gardner et al. |

FOREIGN PATENT DOCUMENTS
| | | |
|---|---|---|
| EP | 1772825 A1 | 4/2007 |
| WO | 2006090309 A2 | 8/2006 |

OTHER PUBLICATIONS

Renault, G., et al., "A posterion navigator echo for perfusion imaging of the liver with contrast ultrasound," 2004 IEEE International Symposium on Biomedical Imaging, Arlington, VA, US, Apr. 15-18, 2004, pp. 316-319.

Xu, Q., et al., "A novel respiratory detection method based on automated analysis of ultrasound diaphragm video," Medical Physics, vol. 33, No. 4, Apr. 2006, pp. 916-921.

*Primary Examiner* — Michael Rozanski

(57) ABSTRACT

An ultrasonic imaging apparatus and method are described for monitoring the progress of therapy for pathology such as lesions, tumors, and metastases by means of contrast agent imaging. A sequence of images are acquired as a bolus of contrast agent infuses the tissue containing the pathology. Time-intensity curves of pathology and normal tissue are produced and used to measure perfusion in the pathology as affected by therapy. The motional effects of respiration can be taken into account during image acquisition by detecting the position of a landmark such as the diaphragm in each of the images of the sequence and discarding from processing those images which exhibit a change in the position of the landmark relative to the probe.

18 Claims, 7 Drawing Sheets

RESPIRATORY-GATED THERAPY ASSESSMENT WITH ULTRASONIC CONTRAST AGENTS

This application claims the priority of international application number PCT/IB2009/050277, filed Jan. 23, 2009, which claims the benefit of U.S. provisional application Ser. No. 61/022,888 filed Jan. 23, 2008, which is incorporated herein by reference.

This invention relates to ultrasonic diagnostic imaging systems and, in particular, to the use of ultrasonic diagnostic imaging systems to assess the progress of therapeutic treatment of tumors.

International patent publication WO 2006/090309 (Bruce et al.) describes an ultrasonic imaging technique for detecting lesions in the liver by use of an ultrasonic contrast agent. A bolus of contrast agent is introduced into the body and the time of arrival of the contrast agent in the liver is detected. When a bolus of contrast agent travels through the blood vessels of the body and begins to appear at a specific organ or location in the body, the build-up of contrast in the images is termed the "wash-in" of the contrast agent. As the infusion of contrast agent plateaus at the location in the body and then declines as it is carried away from the location by the flow of blood, the decline is termed the "wash-out" of the contrast agent. In the aforementioned patent publication the inventors take advantage of the fact that the flow of blood to the liver comes from two sources, the hepatic artery and the portal vein. Since the flow of blood during the first, arterial phase of blood flow will perfuse HCC and metastatic liver lesions first, the inventors identify such lesions by detecting the times of arrival of contrast agent in the liver during the arterial and the later portal phase of blood flow. An area of early wash-in of contrast agent to the liver can be symptomatic of a lesion.

Once a lesion or metastasis has been identified by this and/or other means, a treatment regimen is generally prescribed by a physician. The therapy may involve hyper-/hypothermia, cytotoxic chemotherapy, or anti-angiogenesis agents, for example. The therapy is usually not performed in a single session, but in several sessions over a period of weeks or months. At each therapy session it is generally desirable for a physician to assess the progress of the therapy to determine its effectiveness for the patient. The lesion or metastasis may be imaged diagnostically to see whether it is shrinking, for instance. But often the progress of treatment is slow and only small changes in the lesion or metastasis have occurred since the previous session. In such instances it is desirable to assess the progress of therapy quantitatively by measuring certain characteristics of the tumor. One such measure is the regression of tumor angiogenesis. As a lesion or metastasis shrinks with the necrosis of its cells, the microvasculature which developed to nourish the lesion will provide a smaller supply of blood for the lesion and may itself begin to shrink. One quantitative approach is to assess this regression of angiogenesis, the decline in performance of the lesion's microvasculature. It is desirable that such quantitative measures be repeatable and immune to variations from one imaging procedure to the next, such as variation of the bolus injection, patient cardiac output, and ultrasound machine settings which may differ from one examination day to another. Eliminating the effects of these variations enables the measurements to be comparable from one therapy session to another. It is an object of the present invention to provide new and improved techniques for assessing lesion or metastasis angiogenesis during a period of therapy for the tumor.

In accordance with the principles of the present invention, time-intensity curves of the wash-in and wash-out of ultrasonic contrast agents are produced and used to quantify the tumor angiogenesis resulting from therapy. An image of a lesion or metastasis is acquired by an ultrasonic imaging system and the pathology is continuously imaged as contrast agent washes into and out of the tissue or organ being observed. For an accurate measurement of this process it is desirable to steadily acquire ultrasonic signals from the same location of the metastasis as the contrast agent washes in and out, so that the signal information for time-intensity curve computation continually emanates from the same point of the lesion. In accordance with a first aspect of the present invention, the effects of respiratory motion are removed by respiratory gating of the data acquisition for time-intensity curve production. A preferred technique of respiratory gating is one performed by image analysis, in which the presence or absence of an anatomical landmark in the image, such as the diaphragm, is used to decide whether an image is or is not to be used for time-intensity curve processing.

In accordance with a further aspect of the present invention, a time-intensity curve is produced both for ultrasonic data from the tumor and for ultrasonic data from normal tissue. A wash-in time (WIT) parameter is calculated for each time-intensity curve. A wash-in time ratio (WITR) is formed of the two parameters, which reduces variations in wash-in time quantification due to factors such as bolus differences, cardiac output, and ultrasound system settings. The WITR thus provides an accurate and comparable indicator of the progress of the therapy.

In accordance with yet another aspect of the present invention, the time-intensity curves of the tumor and normal tissue are subtracted from each other to form a differential time-intensity curve. The shape of the differential time-intensity curve and its variations over time are another indicator of the progress of the therapy.

Figure 1:
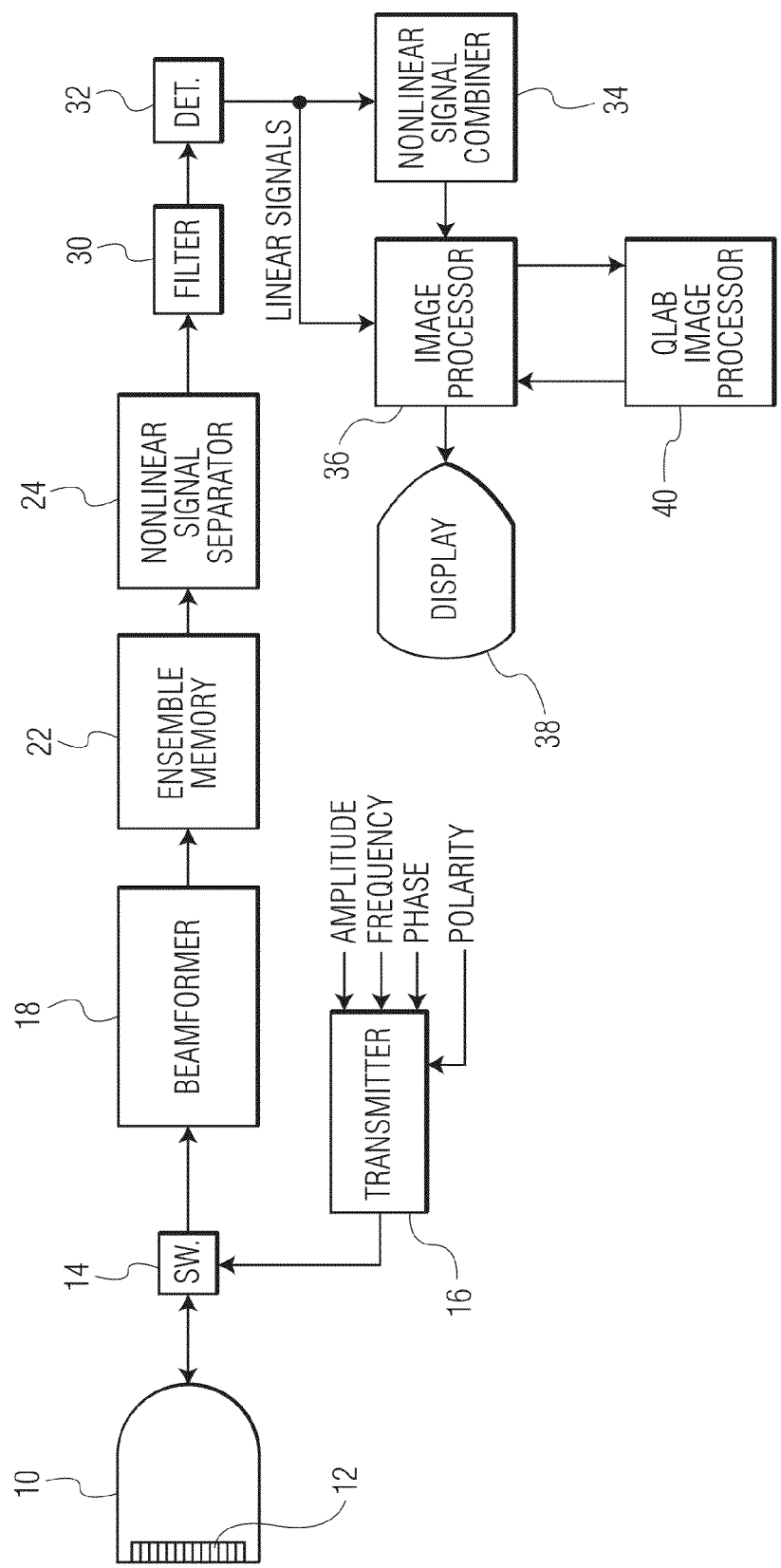
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. This system operates by scanning a two or three dimensional region of the body being imaged with ultrasonic transmit beams. As each beam is transmitted along its steered path through the body, the beam returns echo signals with linear and nonlinear (fundamental and harmonic frequency) components corresponding to the transmitted frequency components. The transmit signals are modulated by the nonlinear response of contrast agent microbubbles encountered by the beam, thereby generating echo signals with harmonic components.

The ultrasound system of FIG. 1 utilizes a transmitter 16 which transmits waves or pulses of a selected modulation characteristic in a desired beam direction for the return of harmonic echo components from scatterers within the body. The transmitter is responsive to a number of control parameters which determine the characteristics of the transmit beams, including the frequency components of the transmit beam, their relative intensities or amplitudes, and the phase or polarity of the transmit signals. The transmitter is coupled by a transmit/receive switch 14 to the elements of an array transducer 12 of an ultrasound probe 10. The array transducer can be a one dimensional array for planar (two dimensional) imaging or a two dimensional array for two dimensional or volumetric (three dimensional) imaging.

The transducer array 12 receives echoes from the body containing fundamental (linear) and harmonic (nonlinear) frequency components which are within the transducer passband. These echo signals are coupled by the switch 14 to a beamformer 18 which appropriately delays echo signals from the different transducer elements then combines them to form a sequence of linear and harmonic signals along the beam from shallow to deeper depths. Preferably the beamformer is a digital beamformer operating on digitized echo signals to produce a sequence of discrete coherent digital echo signals from a near field to a far field depth of the image. The beamformer may be a multiline beamformer which produces two or more sequences of echo signals along multiple spatially distinct receive scanlines in response to a single transmit beam, which is particularly useful for 3D imaging. The beamformed echo signals are coupled to an ensemble memory 22

In the ultrasound system of FIG. 1, multiple waves or pulses are transmitted in each beam direction using different modulation techniques, resulting in the reception of multiple echoes for each scanned point in the image field. The echoes corresponding to a common spatial location are referred to herein as an ensemble of echoes, and are stored in the ensemble memory 22, from which they can be retrieved and processed together. The echoes of an ensemble are combined in various ways by the nonlinear signal separator 24 to produce the desired nonlinear or harmonic signals. For example, two pulses with different phase or polarity modulation can be transmitted to each point in the image field. When the echoes resulting from the two pulses are received by the ultrasound system and additively combined, the different modulation causes the fundamental frequency components of the echoes to cancel and the harmonic components to reinforce each other. This separates out the harmonic components of the echo signals. Alternatively, when the two echoes are subtracted from each other, the fundamental frequency components are reinforced and the harmonic components cancel. This separates out fundamental frequencies for construction of a standard B mode image. This modulation is referred to as "pulse inversion," and can be done by phase, polarity or amplitude modulation as described in U.S. Pat. No. 5,706,819 (Hwang et al.), U.S. Pat. No. 5,951,478 (Hwang et al.), and U.S. Pat. No. 5,577,505 (Brock Fisher et al.)

The separated signals are filtered by a filter 30 to further remove unwanted frequency components, then subjected to B mode or Doppler detection by a detector 32. The detected signals are coupled to a nonlinear signal combiner 34 to reduce image speckle content. The signals are then processed for the formation of two dimensional, three dimensional, spectral, parametric, or other desired image in image processor 36, and the image is then displayed on a display 38. Detected fundamental (linear) signals which do not need speckle reduction processing are coupled directly to the image processor 36 for image formation and display.

In accordance with the principles of the present invention, the ultrasound image data is also coupled to a QLab image processor 40 for the production of time-intensity curves and contrast agent wash-in and wash-out characteristics. The time-intensity curves and characteristics produced by the QLab processor are coupled back to the image processor where they may be displayed numerically or graphically on the display 38 along with the ultrasound images. A standard QLab processor which is suitable for the production of time-intensity curves is available from Philips Healthcare of Andover, Mass.

A standard QLab processor produces the well-known time-intensity curves, also referred to as perfusion curves or reperfusion curves. See U.S. Pat. No. 5,833,613 (Averkiou et al.), international patent publication WO 2005/099579 (Rafter), and international patent publication WO 2005/054898 (Garg et al.) As these publications illustrate, the build-up of contrast agent at points in the tissue (points in the image) is monitored during the arrival of the contrast agent at locations in the body. The amount of contrast agent at a point is indicated by the intensity of echoes returned from contrast agent microbubbles at each point, and is present in a sequence of images acquired by low power (low MI) transmission as the contrast agent washes into the tissue. A time-intensity curve can be formed of this build-up of contrast intensity and its subsequent decline during wash-out of the contrast agent for each point in the tissue which returns the time sequence of echoes frame-by-frame. A qualitative presentation of the time-intensity curves for the entire tissue being viewed can be formed by coloring each pixel in an anatomical image with a color that represents a parameter of the time-intensity curves at each point in the image. The Garg et al. application illustrates the formation of a parametric image of the myocardium where the color of each pixel in the image represents the peak level attained by the time-intensity curve at each point in the myocardium, for example. See also U.S. Pat. No. 6,692,438 (Skyba et al.)

In an implementation of the present invention, contrast agent perfusion echo data is acquired, over a sequence of images as the contrast agent arrives at the location of a metastasis in the body, builds up, and then washes out. The intensity values of the echoes will thus start from a baseline level of no contrast agent present, then rise, plateau, and decline as the contrast agent washes out. A curve-fitting algorithm then fits this data variation to an error function defined as $$I(t)=A[erf\{(t-t_0)/T\}+I_0]$$

where $I(t)$ is the linear intensity at time t, A is the maximum intensity over the baseline offset, T is wash-in time parameter which is linearly proportional to wash-in time (e.g., from 5=8-95%), $I_0$ is baseline offset, and $t_0$ is a time offset. The wash-in time is preferably extracted from the fitted curve instead of the noisy image data. Preferably the contrast agent echo data does not undergo data compression prior to this processing so that the data remains in its acquired linear relationship. Another approach is to fit the whole time-intensity curve (instead of just the wash-in part) to appropriate mathematical models as the log normal distribution for example defined as $$I(t) = \frac{A}{\sqrt{2\pi}\,\sigma(t-t_0)} e^{-\frac{[ln(t-t_0)-\mu]^2}{2\sigma^2}} + C$$

where $\mu$ and $\sigma$ are the mean and standard deviation of the normal distribution from which the logarithmic transformation was obtained. The curve can be scaled horizontally by varying • and changed in terms of skewness by varying •. The area under the curve is A, $t_0$ is the time offset, and C is the baseline intensity offset. The log normal fitted curve is used to extract the wash-in time.

Figure 5:
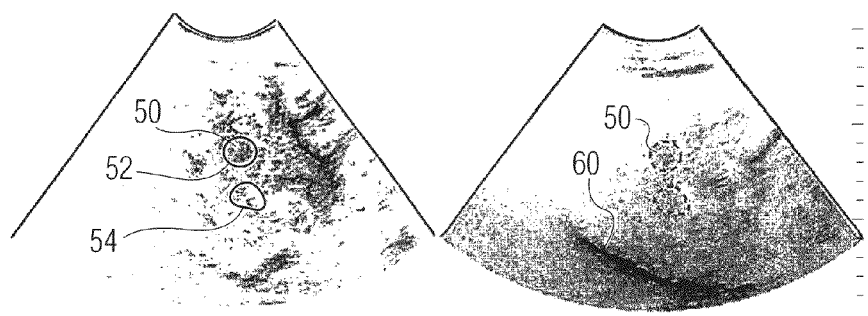
FIG. 5 is an illustration of ROIs for time-intensity curves in accordance with the present invention in an image of the liver acquired during the arterial phase.

FIG. 5 illustrates one pair of images in a sequence of image frames of a metastasis 50 in the surrounding liver tissue. The pair of images are produced from the same echo data, with the left image being a second harmonic image which emphasizes the contrast agent and the right image being a fundamental frequency image of the same anatomy. When the liver is perfused with the contrast agent the perfused metastasis 50 stands out distinctly in the harmonic image and its border can be outlined by a tracing 52. The tracing can be done manually or by automated or semi-automated processing such as border detection, a thresholding process, or a region-growing technique initiated by indication of a seed point on the border of the metastasis. The border tracing 52 thus defines the region of interest (ROI) of the metastasis within its border. It is seen that the metastasis 50 is less distinct in the fundamental B mode image on the right because the harmonic response of the contrast agent is suppressed in this presentation. With the ROI of the metastasis delineated by the border tracing 52, the contrast agent intensity of the metastasis at the time of acquisition of the image can be measured by combining the pixel values within the border 52 by integration, summation, averaging, or other selected combining technique.

Figure 6:
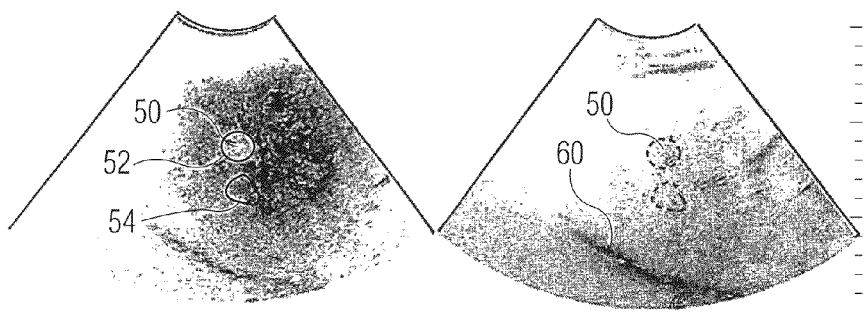
FIG. 6 is an illustration of ROIs for time-intensity curves in accordance with the present invention in an image of the liver acquired during the late portal phase.

The images of FIG. 5 were acquired during the arterial phase of the blood flow to the liver, FIG. 6 is a pair of harmonic and fundamental images of the same tissue and metastasis 50 acquired in the late portal phase. As previously mentioned, HCC and matastatic liver lesions generally receive most of their blood perfusion during the arterial phase, whereas normal parenchyma in the liver receives most of its blood perfusion during the portal phase, as seen by the greater shading of the liver in the left image of FIG. 6. For clarity of illustration the ultrasound images in this application are shown as a black-on-white grayscale rendering rather than the conventional white-on-black.

Figure 2:
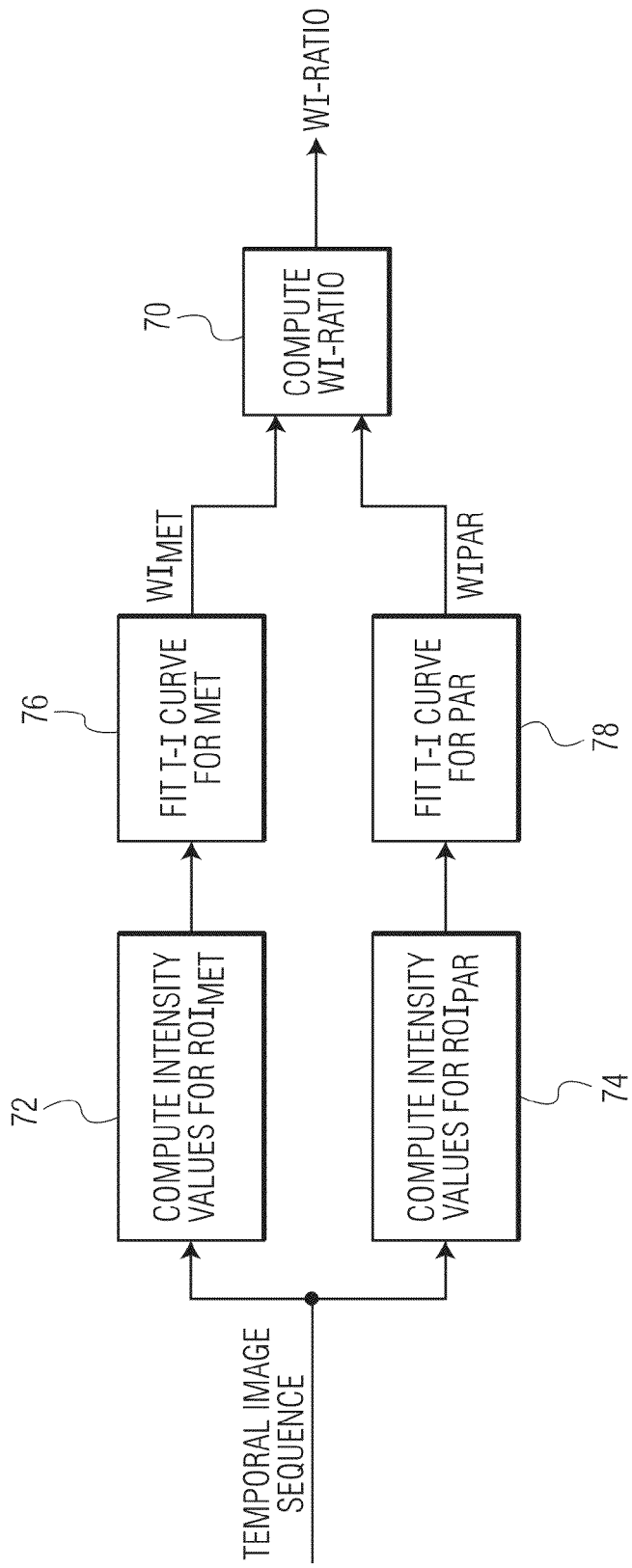
FIGS. 2 and 3 illustrate details of the operation of the QLab processor of FIG. 1 in accordance with the principles of the present invention.
Figure 7:
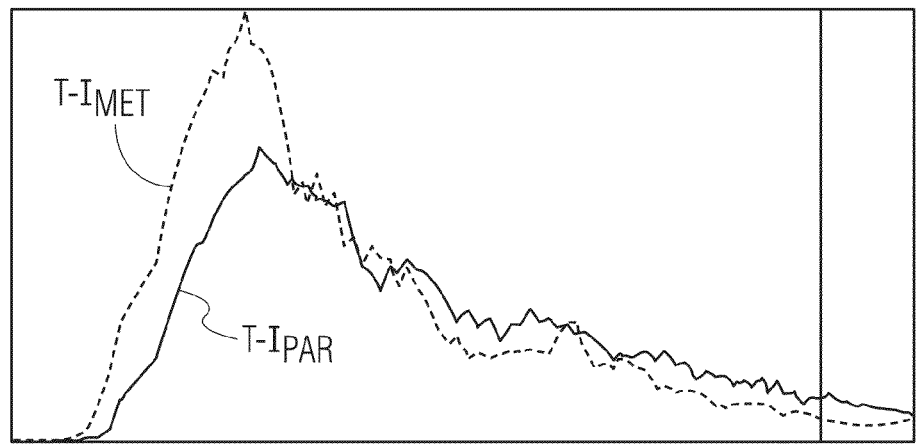
FIG. 7 illustrates time-intensity curves for a metastatic lesion and normal parenchyma.

In accordance with the principles of the present invention, a parameter referred to herein as the wash-in time ratio (WITR) is computed as a quantitative measure of the perfusion of the metastasis. The WITR is computed as shown by the block diagram of FIG. 2. From a temporal sequence of images of a metastasis or lesion during contrast agent wash-in and wash-out as shown by FIGS. 5 and 6, contrast agent intensity values are computed for the $ROI_{Met}$ of the metastasis 50 as indicated by box 72. As explained above, these values can be computed by combing the pixel values of the metastasis ROI for each image of the sequence. In box 74 intensity values are computed for an $ROI_{Par}$ of normal parenchyma of the tissue. This may be done by tracing a region of normal tissue as shown by the tracing 54 in FIGS. 5 and 6, and using the normal tissue perfusion pixel values within this second tracing. These values are therefore perfusion values of normal tissue. In box 76 a time-intensity curve is fitted to the perfusion values of $ROI_{Met}$, and in box 78 a time-intensity curve is fitted to the perfusion values of $ROI_{Par}$. The fit is not always necessary but it gives a better estimation of WITR. While WITR can be measured directly from the data, noise in the data can interfere with the accuracy of the measurement, hence the preference for curve-fitting. FIG. 7 is an illustration of two such time-intensity curves, curve $T-I_{Met}$ from the ROI of a metastasis and curve $T-I_{Par}$ parenchyma. A wash-in time parameter WIT is found for each curve, for example by use of the error function or log normal distribution described above. This determines a wash-in time parameter for both the metastasis and normal parenchyma, $WIT_{Met}$ and $WIT_{Par}$, respectively. A wash-in time ratio WITR is then computed from the two wash-in parameters by dividing $WIT_{Met}$ by $WIT_{Par}$. The effect of normalizing $WIT_{Met}$ by the wash-in time parameter of normal tissue is to reduce or eliminate the effects of variables in the procedure such as bolus size, cardiac output, and ultrasound system settings, which may differ from one therapy session to another. Thus, comparable quantitative measures of the growth or shrinkage of the metastasis as indicated, by its angiogenesis can be produced for each therapy session over the period of weeks or months that the patient is being treated.

Figure 3:
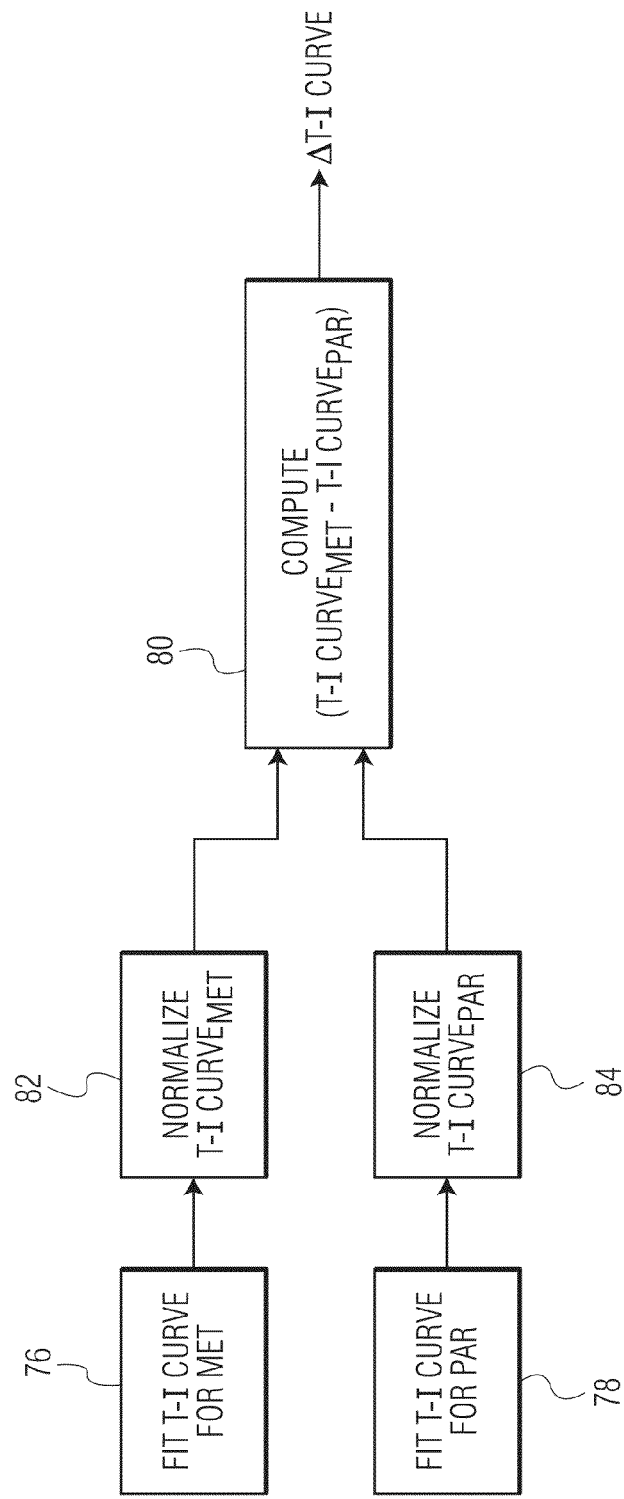
Figure 9A:
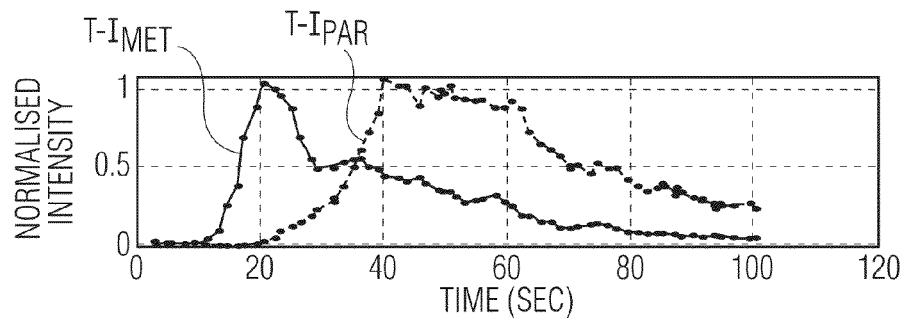
FIGS. 9a-9d illustrate the production and subtraction of time-intensity curves to form a differential time-intensity curve in accordance with the principles of the present invention.
Figure 9B:
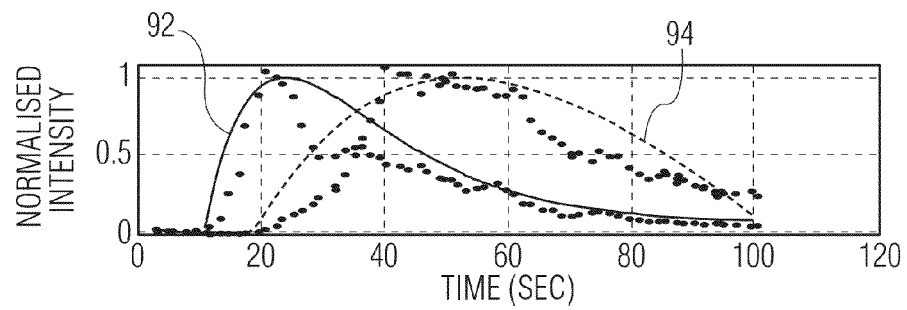
Figure 9C:
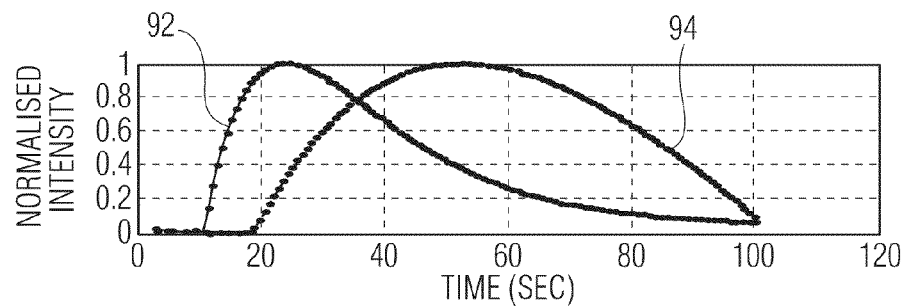
Figure 9D:
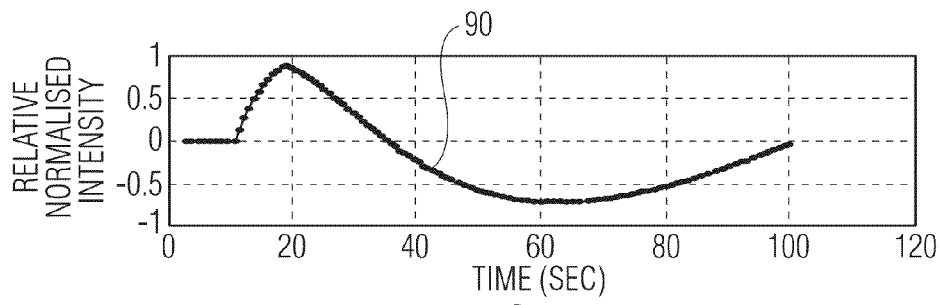

Another quantified measure of metastasis angiogenesis which reduces or removes the effects of bolus injection rate, cardiac output of the patient, or variation in machine settings is illustrated in FIG. 3. A time-intensity curve is fitted for each of the ROIs of the metastasis and the parenchyma as shown in boxes 76 and 78. In boxes 82 and 84, the range of each time-intensity curve is normalized. A convenient normalization scale is zero to one. In box 80 a difference curve ΔT–I Curve is computed as the difference between the two normalized curves $T-I\ Curve_{Met}$ and $T-I\ Curve_{Par}$. This process and its results are illustrated in FIGS. 9a-9d. The dots in FIG. 9a illustrate the perfusion intensity values of a metastasis $(T-I_{Met})$ and normal parenchyma $(T-I_{Par})$ acquired over a one hundred second period of contrast agent wash-in and wash-out. The two sets of values are normalized to the same scale of zero to one, where the peak intensity value of each data set is scaled to the one level. These curves illustrate the characteristic early wash-in of contrast agent during the arterial phase for the metastasis and the later perfusion of the liver parenchyma during the portal phase. In FIG. 9b a curve 92 (for example error function or log normal distribution) is fitted to the perfusion values of the metastasis and a curve 94 is fitted to the perfusion values of the parenchyma. FIG. 9c shows the two curves 92 and 94 in darker lines without the acquired intensity data values. FIG. 9d shows a curve 90 which is the computed difference ΔT–I Curve of the two curves 92 and 94 of FIG. 9c. When the tumor therapy is successful and the angiogenesis of the metastasis declines with treatment, the ΔT–I Curve will show a progressive flattening and will approach a straight line. This is an expected result, for when the lesion has been dissipated its location in the body will respond like normal parenchyma, and the difference of the two (now virtually identical) curves for normal tissue and the lesion location will approach zero. The difference curve could also be expressed as a parameter value such as the maximum slope of the difference curve. When the maximum slope value approaches zero (there is no slope), this is an indication that the difference curve is approaching a straight line.

Figure 4:
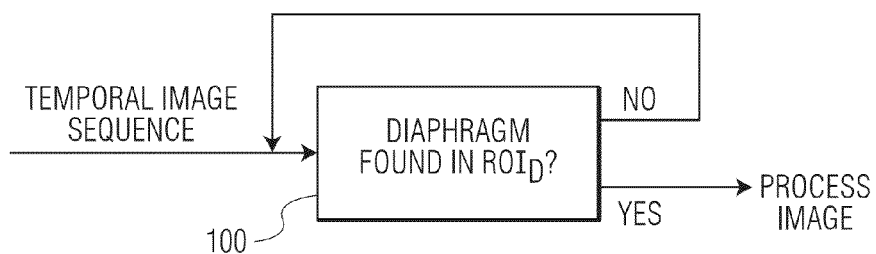
FIG. 4 illustrates respiratory gating through image processing in accordance with the principles of the present invention.
Figure 8:
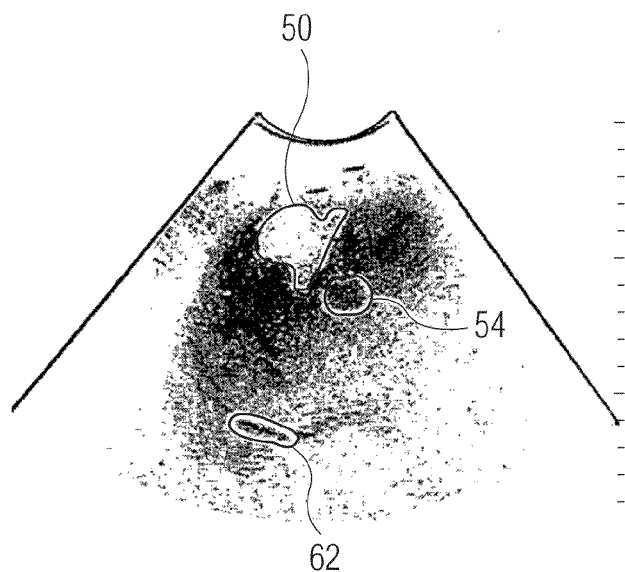
FIG. 8 illustrates the identification of the diaphragm in an ultrasound image for respiratory gating in accordance with the principles of the present invention.

It is seen from the time scale of the graphs of FIGS. 9a-9d that a typical period of contrast agent wash-in and wash-out can last for 100 seconds. This means that a clinician acquiring the image data must maintain the same image of the lesion steadily for 100 seconds so that each intensity value is of the same region of the lesion. If the probe moves during the acquisition, for instance, the lesion can move out of the image plane and the data acquired cannot be used. Even if the probe is held steady against the body of the patient, the lesion, can still move relative to the probe field, of view due to the respiratory motion of the patient. One way to overcome the effect of respiratory motion is to gate the image acquisition to the respiratory cycle. A respiratory signal can be acquired by known means such as an elastic band with strain or pressure sensors around the chest of the patient. Another technique is to transmit small signals between sensors across the chest of the patient and measure the patient's chest impedance variations. These and other techniques can produce cyclical signals of the respiratory cycle and can be used to gate the acquisition of images to the same phase of the respiratory cycle. In accordance with another aspect of the present invention, respiratory gating is performed by image processing as shown in the block diagram of FIG. 4. The fundamental frequency images on the right side of FIGS. 5 and 6 show a distinctly shaded region 60 at the bottom of each image (which would be bright regions in a standard white-on-black grayscale ultrasound image). This image landmark 60 is the diaphragm of the patient in these images. In FIG. 8 the diaphragm in the image has been outlined by a tracing 62. In the illustrated example the tracing 62 is replicated in the same position on each image of the image frame sequence. If the anatomy in the image does not move relative to the probe as the image sequence is acquired, the diaphragm landmark 60 will be present in the tracing outline 62 in each image. However, respiratory motion may move the diaphragm 60 in and out of the tracing, particularly with deep breaths. The image processor 100 of FIG. 4 detects this change by looking for the diaphragm landmark in the same location, $ROI_D$, which is the tracing 62 in the example of FIG. 8. When the diaphragm landmark 60 is found in its expected location in the image ("Yes"), the image is forwarded for processing and quantification. However, if respiratory motion causes the diaphragm landmark 60 to move from its expected $ROI_D$ location in an image ("No"), that image is omitted from processing. This process is applied to all of the images in the sequence so that respiratory motional effects on the imaging of the metastasis, as indicated by movement of the diaphragm, are eliminated by discarding those images which are not consistently aligned to a constant location of the diaphragm. There are also other possible ways of conducting respiratory gating. For example, a time-intensity curve can be formed from an ROI that closely follows a part of the diaphragm and the threshold of the values are detected. Any image whose intensity value is below the threshold is then discarded. Other motion compensation-based algorithms can also detect respiratory motion and gate for it.

Figure 10:
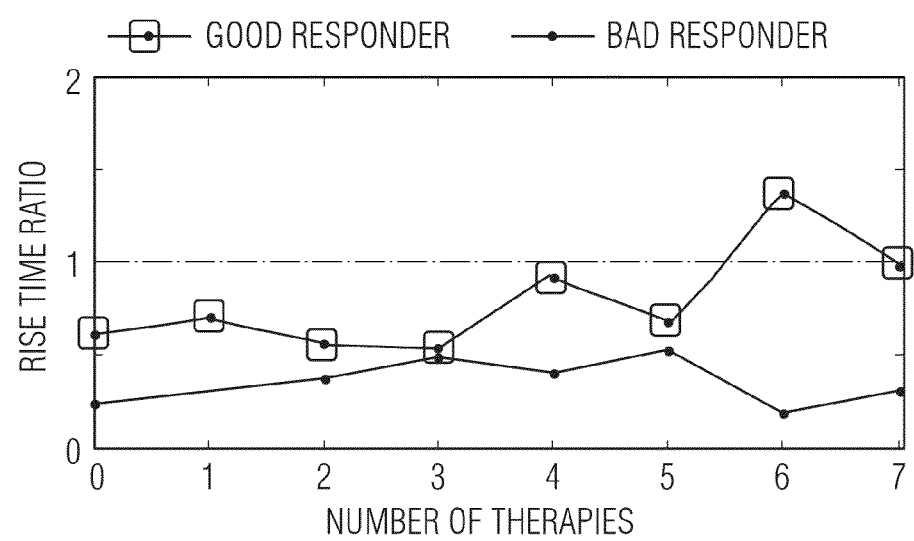
FIG. 10 illustrates the clinical results of assessments of therapeutic progress in accordance with the present invention.

The quantified measurements of the present invention have been used in a clinical environment to monitor the results of tumor treatment of eight patients over three to five therapy sessions. A measurement of the WITR was computed for each patient for each therapy session. Results for a good responder and a bad responder are illustrated in FIG. 10. As this graph shows, the WITR approached unity for the successfully treated patient with each therapy session. For the patient in the group who ultimately failed to respond to treatment (denoted as had responder) the WITR stayed away from unity. It is seen by this graph that WITR measurement is well correlated with actual clinical results of therapy and may be used as a therapy biomarker.

What is claimed is:

1. An ultrasonic diagnostic imaging system for assessing the progress of tumor therapy comprising:
    an ultrasound probe for acquiring a sequence of ultrasound images of a tumor and its adjoining tissue as a contrast agent perfuses the tissue, a plurality of the images further including an anatomical landmark indicative of tissue motion;
    a contrast perfusion processor which processes perfusion parameters from the ultrasound images; and
    an image processor which identifies the anatomical landmark in the sequence of images and enables contrast perfusion processing of images which include the anatomical landmark in the same position in the same plane of each temporally successive image while discarding from processing those images in the sequence which do not include the anatomical landmark in the same position in the same image plane.

2. The ultrasonic diagnostic imaging system of claim 1, wherein the anatomical landmark further comprises a diaphragm.

3. The ultrasonic diagnostic imaging system of claim 2, wherein the location of the diaphragm in the images is indicated by a manual tracing,
    wherein the image processor identifies the presence of image data of the diaphragm in the manual tracing.

4. The ultrasonic diagnostic imaging system of claim 2, wherein the location of the diaphragm in the images is indicated by image processing.

5. The ultrasonic diagnostic imaging system of claim 1, wherein the image processor further operates to identify variation of the location of the anatomical landmark in images of the sequence.

6. The ultrasonic diagnostic imaging system of claim 1, wherein the image processor further operates to omit from processing images in which the anatomical landmark does not appear in a predetermined position.

7. The ultrasonic diagnostic imaging system of claim 1, wherein the contrast perfusion processor further operates to produce a contrast agent wash-in parameter.

8. The ultrasonic diagnostic imaging system of claim 7, wherein the contrast perfusion processor further operates to produce a normalized contrast agent wash-in parameter.

9. A method for ultrasonically monitoring the progress of tumor therapy comprising:
    acquiring a sequence of ultrasound images of a tumor and its adjoining tissue as a contrast agent perfuses the tissue;
    processing the images to identify tissue motion in the images;
    perfusion parameter processing only those images of the sequence which are not adversely affected by tissue motion to determine a perfusion parameter which is a therapy biomarker.

10. The method of claim 9, further comprising omitting from the sequence images which are adversely affected by tissue motion.

11. The method of claim 10, further comprising omitting from the sequence images which are adversely affected by tissue motion as indicated by the location of an anatomical landmark in the images.

12. The method of claim 11, wherein the anatomical landmark is a diaphragm.

13. The method of claim 9, wherein the perfusion parameter is a contrast agent wash-in parameter.

14. The method of claim 13, wherein the perfusion parameter is a normalized contrast agent wash-in parameter.

15. A method for ultrasonically monitoring the progress of tumor therapy comprising:
    acquiring a sequence of ultrasound images of a tumor and its adjoining tissue as a contrast agent perfuses the tissue;

selecting ultrasound images of the sequence for processing by respiratory gating;

extracting from data of the selected images a normalized parameter of the perfusion of the tissue by the contrast agent; and displaying the normalized parameter as a tumor biomarker of the progress of tumor therapy.

16. The method of claim 15, wherein selecting further comprises selecting ultrasound images for processing by means of a respiration sensor.

17. The method of claim 15, wherein respiratory gating further comprises analyzing the data of the acquired images for respiratory effects.

18. The method of claim 15, wherein respiratory gating further comprises analyzing the data of the acquired images for respiratory motion.

* * * * *